(12) United States Patent
Källander et al.

(10) Patent No.: US 7,566,529 B2
(45) Date of Patent: Jul. 28, 2009

(54) METHOD FOR THE RECOVERY OF RETROVIRAL REVERSE TRANSCRIPTASE (RT) ACTIVITY FROM A SAMPLE CONTAINING UNPROTECTED CELLULAR POLYMERASES

(75) Inventors: Clas Källander, Uppsala (SE); Simon Gronowitz, Uppsala (SE); Tommy Gatu, Uppsala (SE)

(73) Assignee: Cavidi Tech AB, Uppsala (SE)

( * ) Notice: Subject to any disclaimer, the term of this patent is extended or adjusted under 35 U.S.C. 154(b) by 616 days.

(21) Appl. No.: 10/472,756

(22) PCT Filed: Mar. 27, 2002

(86) PCT No.: PCT/SE02/00612

§ 371 (c)(1),
(2), (4) Date: Oct. 3, 2003

(87) PCT Pub. No.: WO02/082088

PCT Pub. Date: Oct. 17, 2002

(65) Prior Publication Data

US 2004/0110265 A1    Jun. 10, 2004

(30) Foreign Application Priority Data

Apr. 5, 2001    (SE) .................................. 0101219

(51) Int. Cl.
*C12Q 1/70* (2006.01)
(52) U.S. Cl. .......................................... 435/5
(58) Field of Classification Search ........ 435/5
See application file for complete search history.

(56) References Cited

FOREIGN PATENT DOCUMENTS

| EP | 0186526 A1 | 2/1986 |
|----|-----------|--------|
| EP | 0 186 526 A1 | 7/1986 |
| WO | WO 01/75147 A1 | 10/2001 |
| WO | 0175147 A1 | 11/2001 |

OTHER PUBLICATIONS

Frederick M. Boyce et al., "New Way to Isolate Simian Virus 40 Nucleoprotein Complexes from Infected Cells: Use of a Thiol-Specific Reagent", Journal of Virology, vol. 42, No. 1, Apr. 1982, pp. 292-296.

Tom Maudru et al., "Elimination of background signals in a modified polymerase chain reaction-based reverse transcriptase assay", Journal of Virological Methods, vol. 66, 1997, pp. 247-261.

F.M. Boyce, et al. "New Way to Isolate Simian Virus 40 Nucleoprotein Complexes from Infected Cells: Use of a Thiol-Specific Reagent", Journal of Virology, Apr. 1982, vol. 42, No. 1, pp. 292-296.

T. Maudru, et al., "Elimination of background signals in a modified polymerase chain reaction-based reverse transcriptase assay", Journal of Virological Methods, 1997, vol. 66, pp. 247-261.

*Primary Examiner*—J. S. Parkin
(74) *Attorney, Agent, or Firm*—Bacon & Thomas, PLLC (57) ABSTRACT

A method of recovering an enzyme activity, such as reverse transcriptase (RT) activity, from enveloped viruses, such as HIV, in a biological sample containing a non-protected enzymes, is described. A cysteine-modifying substance is used to destroy the activity of the non-protected enzymes, followed by removal of the enveloped virus particles or inactivation of the cysteine-modifying substance with a chemical. Then the virus envelope is lysed and the released enzymes are recovered. Commercial packages containing written and/or data carrier instructions and some chemicals for performing laboratory steps for recovery of an enzyme activity from enveloped viruses, are also disclosed.

9 Claims, 6 Drawing Sheets

METHOD FOR THE RECOVERY OF RETROVIRAL REVERSE TRANSCRIPTASE (RT) ACTIVITY FROM A SAMPLE CONTAINING UNPROTECTED CELLULAR POLYMERASES

The present invention relates to a method of recovering enzyme activity from enveloped viruses, i.e. measurement of enzymes packed in enveloped viruses. The method is particularly developed for biological samples containing non-protected enzymes in addition to the enveloped viruses.

BACKGROUND

A classical example of the problems in this field is encountered during the determination of retroviral reverse transcriptase (RT) in cell extracts or cell culture fluids. During reverse transcription the RT produces a DNA copy of the viral RNA. A conventional RT activity assay is performed by utilizing an artificial template-primer construction and tritiated deoxynucleotide triphosphate as nucleotide substrate. The template/primer pair poly(rA)/oligo(dT) is the most efficient and most used combination for determination of HIV as well as for other retroviral RTs (Baltimore-71, Lee et al-87). It was early recognized that some cellular DNA polymerizing enzymes obscured the results of this type of assay system by producing measurable product amounts.

At least nine different types of DNA polymerases have been identified in eukaryotic cells. Polymerase $\alpha$ is considered to be responsible for DNA replication during cell division, $\beta$ is regarded as being the major polymerase involved in repair of DNA and $\lambda$ is responsible for DNA synthesis in mitochondria. Each of the cellular polymerases occurs in different forms and with different associated proteins. Their enzymatic properties vary both with their molecular form and with cell type origin (for a review see Hübscher et al 2000). In addition, cells may contain enzymes derived from infecting viruses or endogenous virus genes that encode viral DNA polymerase. Of the cellular DNA polymerases, DNA polymerase $\alpha$ is least prone to utilize prA as template, but there are certain molecular species of this enzyme that can efficiently copy prA (Goulian & Grimm 1990, Yoshida et al 1981).

In effect the different polymerases represent a specificity problem during quantification of retroviral RT. Many methods to circumvent this problem can be found in the literature. The most obvious approach is to separate the virus from the cellular proteins. Various methods such as centrifugation or adsorption of virions to specific receptors or antibodies have been used in this context. A common problem occurring when purifying material containing large amounts of cellular components and minute quantities of virus is that co-purification of small amounts of cellular polymerase cannot be excluded. Furthermore, from a practical point of view it is not attractive to process large amounts of samples with relatively cumbersome separation procedures.

Another approach is to design isozyme specific enzyme assay conditions which more or less exclude cellular polymerase, i.e. $\lambda$ polymerase, from detection. This can be achieved by using inhibitors, alternative metal ions or template/primer pairs. For example poly(2'-0-methyl-rC)$_n$ oligo (dG)$_{12-18}$ is known to be a highly specific substrate for retroviral RTs. The increased specificity achieved by this type of method is, however, usually hampered by the corresponding decrease in reaction velocity and subsequent reduction in detection sensitivity for the enzyme that is intended to be measured.

We have recently developed a method for quantification of HIV RT in plasma sampled from infected persons. The method is based on binding of the virus to a gel with an immobilized ion exchanger. Antibodies and disturbing substances are removed by a wash and enzymatically active RT is recovered by lysis of the immobilized virus with non-ionic detergent (Gatu et al 2000). The amount of RT recovered is finally quantified with a sensitive RT assay based on the use of immobilized prA primed with odT. When processing control plasma from healthy blood donors in this system we found small amounts of RT activity in the purified fractions.

Further investigations revealed that crude EDTA plasma from healthy humans contained comparatively large amounts of this activity, which also was abundant in extracts from the lymphocyte fraction of the same type of samples. Some characteristics of this unclassified enzyme are depicted in Table 1. The amount of activity recovered from our separation system after "virus immobilization" was less than a thousandth part of the total activity in plasma but enough to severely obscure the detection of small amounts of HIV RT.

DESCRIPTION OF THE INVENTION

The present invention provides a solution to the above disclosed specificity problem, but is also generally applicable to detection of all enzymes contained in enveloped viruses. Examples of enveloped virus families and some human species within the families include Poxviridae, e.g. vaccinia and smallpox, Iridoviridae, Herpesviridae, e.g. Herpes simplex, Varicella virus, cytomegalovirus and Eppstein-Barr virus, Togaviridae, e.g. Yellow fewer virus, thick-borne encephalitis virus, Rubella virus and tropical encephalitis virus, Coronaviridae, e.g. Human coronovirus, Paramyxoviridae, e.g. Parainfluenza, mumps virus, measles virus and respiratory syncytial virus, Rabdoviridae, e.g. vesicular stomatitis virus and rabies virus, Filoviridae, e.g. Marburg virus and Ebola virus, Orthomyxoviridae, e.g. Influenza A and B viruses, Bunyaviridae, e.g. Bwamba virus, California encephalitis virus, sandfly fever virus and Rift Valley fever virus, Arenaviridae, e.g. LCM virus, Lassa virus and Juni virus, Hepnadnaviridae, e.g. hepatitis B-virus, and Retroviridae, e.g. HTLV and HIV.

The method of the invention is based on the use of a protein-modifying chemical to destroy the activity of non-protected soluble enzymes, i.e. free enzymes and enzymes associated with e.g. proteins, cell components or organelles but not protected by a viral envelope. The capacity of a chemical to penetrate the viral envelope is related to its hydrophobic properties. Provided that the viral envelope gives protection to the action of the chemical chosen, it is possible to remove or alternatively inactivate the reactive chemical, lyse the virion and quantitate the activity of the released viral enzyme. There are a host of more or less site-specific reagents for protein modification available (for a review se Means & Feeney 1990).

For the method of the invention, cysteine-modifying substances have been selected as protein-modifying chemicals to destroy the activity of non-protected enzymes. Sensitivity to N-ethyl malemide has been widely used for classification of cellular DNA polymerases. The agent is usually added directly to the reaction mixture and efficiently "inhibits" all mammalian DNA polymerases except DNA polymerase $\beta$. The amount of cysteines in the consensus amino acid sequence of the different retroviral RTs varies considerably i.e. HIV 1 RT has only 2, HIV 2 has 3, Mouse Leukemia Virus (MULV) has 8, while avian myeloblastosis/sarcoma virus has 12 cysteines in the $\beta$ subunit. The sensitivity of the viral RTs to cysteine modification can thus be expected to vary considerably. The effects of modification of the cysteine residues in the HIV RTs have been explored and at least the DNA polymerase activity of both HIV 1 and HIV 2 RT were quite resistant (Hizi et al 1992). Taking the enormous variation recorded among different HIV strains into account this is, however, not likely to be true for all HIV isolates.

More specifically, the present invention is directed to a method of recovering an enzyme activity from enveloped viruses in a biological sample containing non-protected enzymes, comprising the steps of a) incubating the biological sample with a cysteine-modifying substance to destroy the activity of the non-protected enzymes while retaining the viral enzyme activity within the virus envelope, b1) removing the enveloped virus particles from the incubation mixture, or b2) inactivating the cysteine-modifying substance with an inactivating substance retaining the virus envelope from lysis, c) lysing the virus envelope with a lysing buffer to release the virus enzymes, and d) recovering the released virus enzyme from the lysing buffer.

In an embodiment of the method of the invention the enveloped viruses are selected from the family Retroviridae, and are especially selected from Lentiviruses, HTLV/BLV viruses, mammalian D-type retrovirus and mammalian C-type retrovirus.

In a presently preferred embodiment the Lentivirus is human immunodeficiency virus (HIV).

In another embodiment the recovered viral enzyme activity is reverse transcriptase (RT) activity.

In yet another embodiment of the method of the invention the biological sample is a sample of body fluid. Examples of body fluids are urine, sputum, cerebrospinal fluid, synovial fluid, pleural fluid, ascites fluid, and particularly blood, plasma and serum.

In a further embodiment of the method of the invention the cysteine-modifying substance is a water-soluble non-lipophilic substance, such N-ethylmalemide, Thimerosal, p-hydroxymercuribenzoate, 5,5'-dithiobis-(2-nitrobenzoic acid), 2-aminoethyl 2'-aminoethane-thiolsulfonate, 2-nitro-5-thiocyanobenzoic acid, and methyl methane-thiosulfonate.

In still another embodiment the inactivating substance is a mild low molecular weight reducing agent, such as cysteine, cysteamine, mercaptosuccinic acid, or glutathione.

The invention is also directed to a commercial package containing written and/or data carrier instructions for performing laboratory steps for recovery of an enzyme activity from enveloped viruses present in a biological sample, and a cysteine-modifying substance, such as N-ethylmaleimide, phenylmercuric acetate, Thimerosal, p-hydroxy-mercuribenzoate, or 5,5'-dithiobis-(2-nitrobenzoic acid). Optionally the package also contains a virus-binding matrix, such as an anion exchanger matrix, or a substance inactivating the cysteine-modifying substance while retaining the virus envelope from lysis, such as cysteine, cysteamine, mercaptosuccinic acid, or glutathione, and a lysing, buffer, such as an enzyme assay compatible buffer including a detergent.

The invention will now be illustrated by a general description of experiments, examples and drawings, but it should be understood that the invention is not limited to the disclosed embodiments.

General Description of Experiments

The following procedures are intended to illustrate the invention without limiting its use. Two different embodiments of the invention may be used for different purposes. Protocol I) is primarily used for samples containing enzyme activity blocking antibodies (i.e. HIV patient plasma after seroconversion) that must be removed before determination of viral enzyme activity. The polymerase inactivation step in the protocol below is performed in a separate incubation. It can also alternatively be done during the same step when the virion binds to the gel. This is carried out either by adding the cysteine-modifying substance directly to the plasma/gel slurry mixture or by first binding the substance to the gel and then adding the plasma samples. The concentration of substance required may vary with the procedure. Protocol II) can be used for samples essentially free from disturbing factors such as enzyme blocking antibodies, e.g. HIV acute stage sera.

I) Protocol for determination of retroviral RT from material which contains RT blocking antibodies, based on destruction of soluble cellular enzymes followed by isolation of viral RT from mini columns 1) Label the 5 ml plastic tubes to be used. Place them in a Nalgene box. Add 1 ml of sample (e.g. EDTA plasma from HIV infected individuals) to each labelled tube. Add 100 μl of a 66 mM solution of 5,5'-dithiobis-(2-nitrobenzoic acid) in buffered water, vortex and incubate the samples for one hour at room temperature.

The activity of the free plasma enzymes is destroyed during this procedure while the enzymes contained within the virions remains intact. The virions can then be purified from 5,5'-dithiobis-(2-nitrobenzoic acid), enzyme activity blocking antibodies and other substances that may interfere with quantification of viral RT by several separation procedures. The protocol below is based on use of Fractogel® EMD TMAE Hicap gel.

2) Suspend the separation gel carefully and transfer 1500 μl gel slurry to each sample pre-treatment tube.

3) Incubate the samples with the gel slurry for one hour at room temperature with the tubes lying down on an orbital shaker.

4) Label the desired number of 15 ml plastic mini columns to identify the samples being analyzed. Mount the columns in a column washing device e.g. a Supelco Visiprep solid phase extraction vacuum manifold. Transfer the contents in the binding tubes to their corresponding columns. Before transfer vortex the tube briefly to distribute the gel evenly.

5) When all the columns are filled, apply the vacuum and suck the gels dry. Turn off the vacuum and start the washing by filling each column with 9 ml buffer A. When all columns have been filled, apply the vacuum and suck the gels dry.

6) Repeat step 5 three more times, giving a total of four washes. Suck the gels dry after each wash. After sucking the gels dry after the 4:th wash, turn off the vacuum and proceed to step 7.

The washing step removes unbound RT blocking antibodies and 5,5'-dithiobis-(2-nitrobenzoic acid), from the system.

7) Add to all dry gels 9 ml of conditioning buffer (B). Apply vacuum and suck the gels dry.

8) Repeat step 7. Before turning off the vacuum control that all conditioning buffer (B) has been removed from all gels.
9) Lift off the upper part of the column wash device. Mount the tube holder with the labelled tubes into a clean container. Refit the upper part of the device. Control that the small tubings from each column go down in their corresponding tubes.
10) Add 300 μl lysis buffer (C) to each column. Let the buffer stand in the column for five minutes. Then, apply the vacuum slowly and suck the gels dry. This will give approximately 300 μl of virus lysate in each tube.

The RT activity recovered in the lysates from step 10 are essentially free from RT blocking antibodies and cellular polymerase activity, and can be quantified with a sensitive RT activity assay, e.g. the Cavidi HS-kit Lenti RT, which is based on the method described by Ekstrand et al 1996.

Note: RT enzymes that are not sensitive to cysteine-modifying substances e.g. wild type HIV 1 RT can optionally be assayed in the presence of up to 5 mM 5,5'-dithiobis-(2-nitrobenzoic acid).

Sensitive enzymes such as MuLV RT and RT from certain therapy resistant HIV 1 strains on the other hand require addition of a sulfhydryl reducing agent, e.g. cysteine or cysteamine, to the lysis buffer.

II) Protocol for determination of RT activity in samples essentially free from enzyme blocking antibodies, e.g. HIV acute stage plasma or virus culture supernatant, based on inactivation of soluble cellular enzymes followed by inactivation of 5,5'-dithiobis-(2-nitrobenzoic acid).

1) 200 μl samples (e.g. HIV acute stage plasma) is mixed with 20 μl 33 mM 5,5'-dithiobis-(2-nitrobenzoic acid) in buffered water. The samples are incubated on an orbital shaker at room temperature for one hour.
2) A sulfhydryl reducing agent, e.g. 20 μl of 33 mM cysteamine in water is added and the samples are incubated on an orbital shaker at room temperature for another 30 minutes.
3) Make four fold serial dilutions of the samples in an RT assay compatible buffer containing a detergent e.g. triton X-100. The virions are, now lysed and the RT activity at each dilution can be determined utilizing a sensitive RT assay e.g. the Cavidi HS-kit-Lenti RT.
4) The amount of RT activity in the original sample is calculated from the values in the dilution range were there is a linear relationship between sample dilution and amount of product formed.

EXAMPLES

Materials

Separation gel: e.g. Fractogel® EMD TMAE or Fractogel® EMD TMAE Hicap in 200 mM (2-(N-Morpholino)ethanesulfonic acid) (MES) pH 5.4, 275 mM Potassium iodide and Heparin 80 IU/ml.
Mini columns e.g. Biorad Poly-Prep® (7311553)
Mini column washing device e.g. Supelco Visiprep solid phase extraction vacuum manifold.
Plastic tubes e.g. Nunc 4.5 ml cryogenic tubes.
Cysteine-modifying agent, e.g. 66 mM 5,5'-dithiobis-(2-nitrobenzoic acid) in water buffered with 0.4 M Tris(hydroxymethyl)aminomethane (pH 6.8).
Mild sulfhydryl reducing agent, e.g. 33 mM cysteamine in water.
Wash buffer (A): 20 mM MES pH 6.0, 500 mM Potassium acetate (KAc).
Conditioning buffer (B): A RT assay compatible buffer e.g. 10 mM (N-(2-Hydroxyethyl-piperazine-N'-(2-ethanesulfonic acid) (Hepes) pH 7.6, 25 mM KAc, 20 mM magnesium chloride ($MgCl_2$), 0.2 mM EthyleneGlycol-bis(β-aminoethyl Ether) N,N,N',N'-Tetraacetic Acid (EGTA), 2 mM spermine and 0.5 mg/ml heat inactivated bovine serum albumin.
Lysis buffer (C): A RT assay compatible buffer including a detergent e.g. 1% t-Octophenoxypolyethoxyethanol (Triton X-100), an enzyme stabilizer e.g. 13 ng/ml oligo($dT_{22}$), 0.025 mg/ml Dextran sulfate and the same components as in the conditioning buffer (B). A sulfhydryl reducing agent, e.g. 0.2 mM cysteamine is optionally added when processing viruses with RT that are sensitive to SH oxidation/modification.

Example 1

Some Properties of a DNA Polymerase from Human Plasma

The effect of addition of indicated components to RT reaction mixture devoid of primer (Cavidi HS-kit Lenti RT) was investigated. EDTA plasma from two healthy blood donors (1 μl/assay), recombinant HIV 1 RT or FIV RT of cell culture origin was used as enzyme. The results are presented in Table 1.

The human plasma polymerase activity was dependent on primer, sensitive to inhibition by the ddNTP complementary to the template, but not sensitive to pyrophosphate analogues.

Example 2

The Capacity of Various Cysteine-modifying Agents to Destroy the Activity of Human Plasma Polymerase Fifty µl samples of human EDTA plasma were mixed with 50 µl samples from a serial dilution of each substance. The samples were incubated for one hour on an orbital shaker. Each sample was then diluted twenty times and the residual polymerase activity was measured with Cavidi® HS kit Lenti RT. The polymerase activity at each substance concentration was recalculated into percent of a control consisting of plasma incubated in absence of modifying substance, plotted towards substance concentration and the substance concentration required for 50% activity reduction was determined from the plot.

HIV virus in human plasma devoid of endogenous RT activity was treated with 5 mM of indicated substance according to "Protocol for determination of retroviral RT from material which contains RT blocking antibodies". The recovery of HIV RT was determined with Cavidi® HS kit Lenti RT. The results are given in Table 2.

Example 3

Effect of Incubation with Thimerosal on Different Polymerases in Serum/Plasma

Recombinant wild type HIV 1 RT (■), Recombinant RT from a Nevirapine resistant HIV 1 mutant (Y181C) (◇), Jaagsiekte virus (JSV) RT from a sheep lung cancer (▲), Feline Leukaemia Virus (FIV) RT (○), Bovine Leukaemia virus (BLV) RT (♦) and Porcine Endogenous Retrovirus (PERV) RT (●) derived from cell culture were dilute in heat inactivated foetal calf serum. The different virus enzyme preparations and an EDTA plasma sample from a healthy blood donor (□) were incubated with indicated thimerosal concentration at room temperature (22° C.) for 60 minutes. All the samples were diluted 100 fold in an RT assay compatible buffer and the residual RT activity in each sample was then determined. Three RT assays, each adapted to the type of RT measured were used: HIV 1, JSV, and FIV RTs were measured with Cavidi® HS kit Lenti RT BLV RT with Cavidi® HS kit HTLV RT and PERV and human plasma RT with Cavidi® HS kit $Mn^{2+}$ RT. The results are presented in a diagram in FIG. 1.

Figure 1:
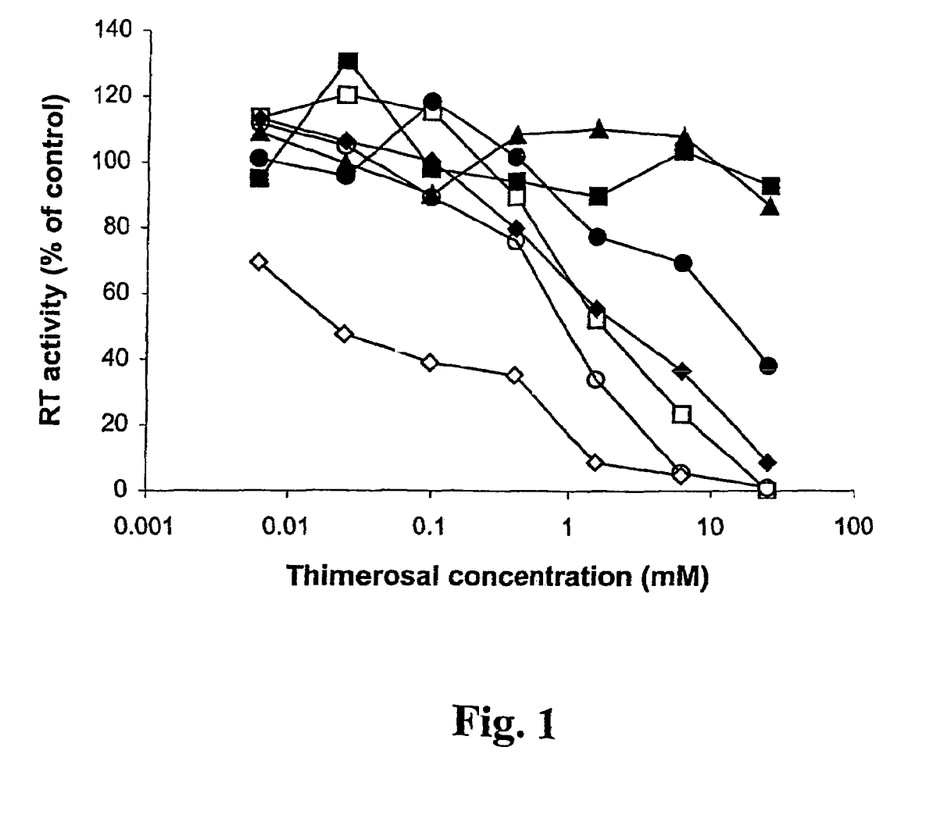
FIG. 1 is a diagram that shows the effect of preincubation with thimerosal on activity of different polymerases in serum/plasma. Recombinant wild type HIV 1 RT (■), Recombinant RT from a HIV 1 mutant (Y181C) (◇), Jaagsiekte virus RT (▲), FIV RT (○), Bovine Leukaemia virus (BLV) RT (◆), Porcine Endogenous Retrovirus (PERV) RT ( ) and a plasma sample from a healthy blood donor (□).

The seven enzymes investigated showed strikingly different sensitivity to thimerosal treatment. The HIV 1 Y181C mutant RT and the FIV RT was the most sensitive enzymes. The thimerosal concentration required for significant enzyme destruction increased among human plasma RT, BLV RT and PERV RT. Two enzymes, the wild type HIV 1 RT and the JSV RT, were totally resistant.

Example 4

Recovery of Viral RT Activity from FIV Spiked Plasma and Selective Destruction of Endogenous RT Activity EDTA plasma with disrupted lymphocytes from a healthy blood donor and FIV diluted in inactivated foetal calf serum (totally devoid of plasma RT activity) were incubated for 1 hour at room temperature with indicated concentration of: A) 5,5'-dithiobis-(2-nitrobensoic acid), B) thimerosal. The samples were separated according to "Protocol for determination of retroviral RT from material which contains RT blocking antibodies". The RT activities recovered were determined with an RT assay (Cavidi HS-kit Lenti RT). Each activity was recalculated into percentage of an identically processed control consisting of the same preparation incubated without any sulfhydryl reactive substance. The recovery of FIV RT from this control was 74% of the activity in the original sample, the corresponding figure for human plasma RT was 0.015%. See FIG. 2, wherein the left columns are blood donor plasma and the right columns are FIV virus in foetal calf serum.

Figure 2:
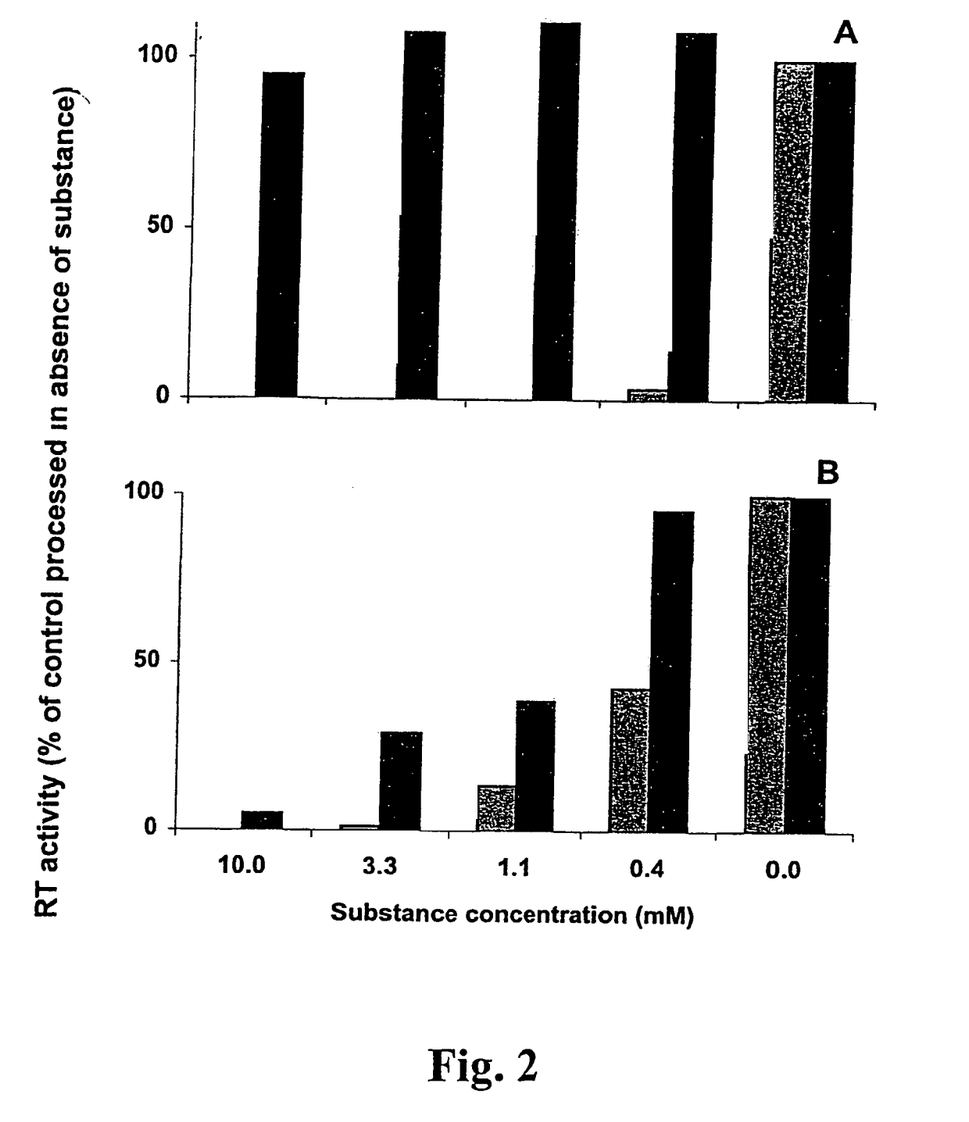
FIG. 2. shows two diagrams A and B of recovery of viral RT activity from FIV spiked plasma and selective destruction of endogenous RT activity. EDTA plasma with disrupted lymphocytes from a healthy blood donor (the left columns) and FIV diluted in inactivated foetal calf serum (the right columns) incubated with: A) 5,5'-dithiobis-(2-nitrobenzoic acid), and B) thimerosal. The RT activities recovered were plotted towards substances concentration.

Incubation with 5,5'-dithiobis-(2-nitrobensoic acid) at concentrations above 0.4 mM totally eliminated the human plasma RT activity without decreasing the recovery of FIV virion associated RT.

Higher concentrations of Thimerosal (>3 mM) were required to achieve a similar effect on the plasma RT. Thimerosal in this concentration range significantly reduced the recovery of FIV RT.

Example 5

Elimination of Polymerase Activity in Plasma Samples from Healthy Blood Donors

Figure 3:
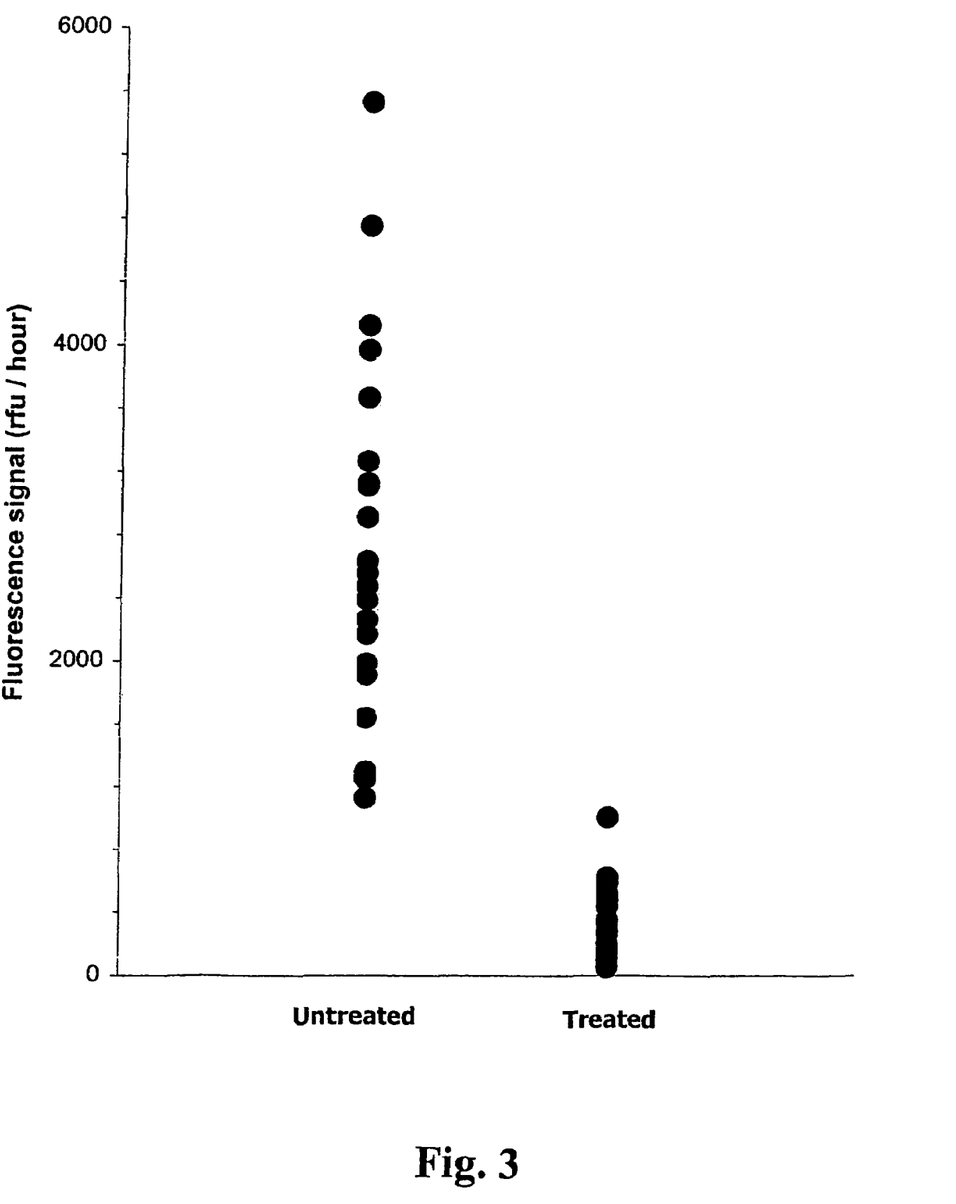
FIG. 3 is a diagram that shows elimination of polymerase activity in plasma samples from healthy blood donors.

Two duplicate sets of 1 ml samples of EDTA plasma from 21 healthy blood donors were processed according to "Protocol for determination retroviral RT from material which contains RT blocking antibodies". The 5,5'-dithiobis-(2-nitrobensoic acid) treatment (step A) was omitted for one sample set and included for the other. The amount of RT activity recovered from each sample was determined using an overnight RT assay using Cavidi® HS kit Lenti RT. See FIG. 3, wherein the left hand groups indicate untreated samples processed according to the protocol. The right hand groups are the same samples processed after treatment. Separation controls e.g. separation of sample application buffer gave values between 262 and 1100 rfu/hour. The detection range of the fluorimeter was up to approximately 1800 000 rfu.

Example 6

Figure 4:
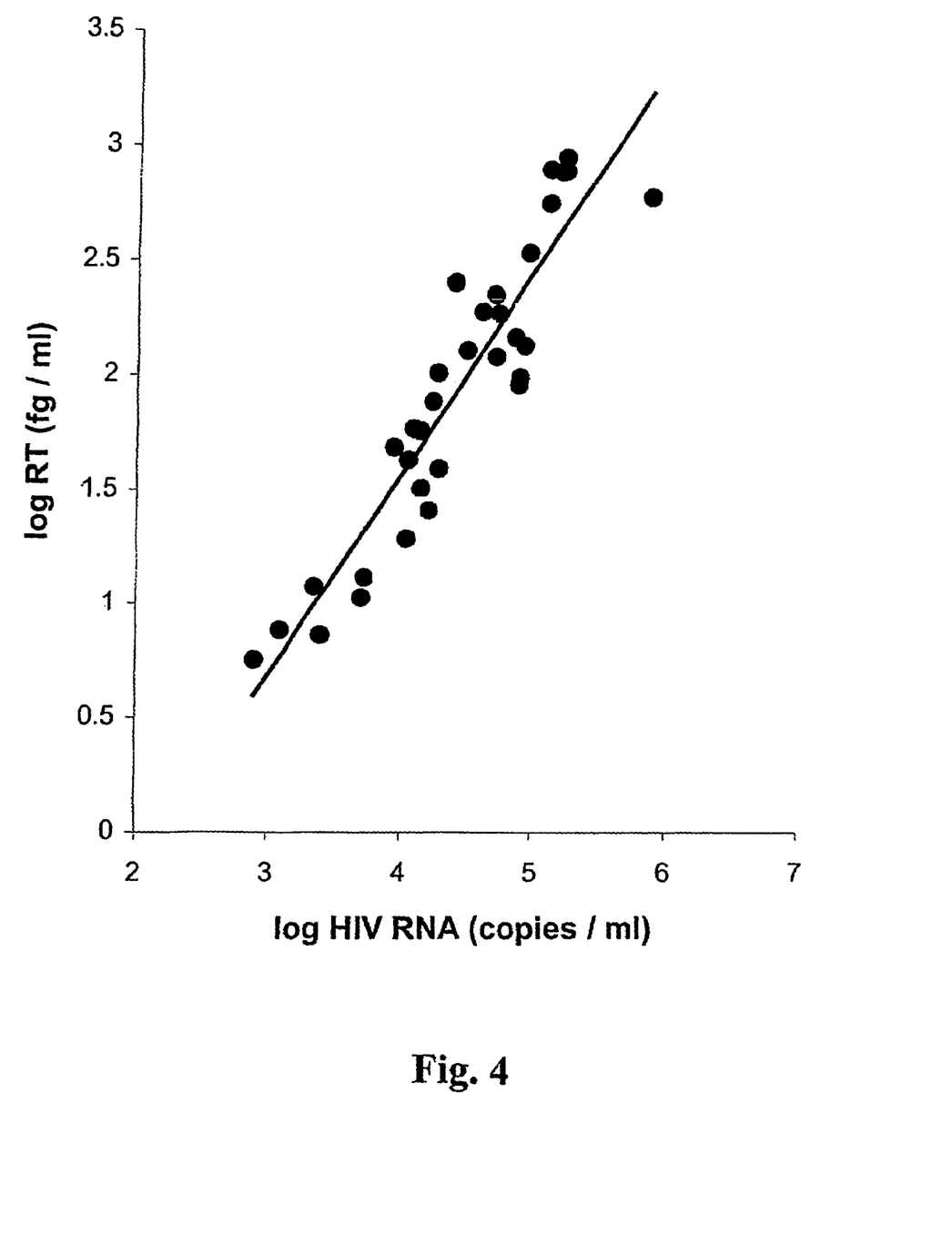
FIG. 4 shows a diagram of a correlation between HIV RT recovered from human plasma according to the invention and viral RNA measured with RNA PCR.

Correlation between HIV RT Activity Recovered from Human Plasma According to the Invention and Viral RNA Measured with RNA PCR 1 ml samples of EDTA plasma from HIV infected individuals were processed according to "Protocol for determination retroviral RT from material which contains RT blocking antibodies" and the amount of RT activity recovered from each sample was determined in an overnight RT assay using Cavidi® HS kit Lenti RT. The RT activities obtained were recalculated into pg HIV 1 RT according to a standard curve. The amount of HIV 1 RNA in each sample was measured by standard HIV 1RNA PCR (Roche, Amplicore). The plot given in FIG. 4 is restricted to samples with a PCR value >500 copies/ml.

A strong correlation was found between amount of plasma RT recovered according to the invention and amount of HIV RNA measured with PCR (r=0.93, n=33, p<<0.001).

Example 7

Alternative Protocol for Treatment of Plasma Samples from HIV Infected Patients

The polymerase inactivation step in "*Protocol for determination of retroviral RT from material which contains RT blocking antibodies*" was performed in four ways: A) In a separate incubation of plasma and substance. B) In the same incubation as when the virion binds to the gel. C) The substance was included in the gel slurry during storage and the pre-treated gel was used for RT isolation. D) The substance was first bound to the gel, unbound substance was removed by a wash and the treated gel was used according to the protocol. The results are presented in FIG. 5. Plasma RT activity (♦), HIV RT activity (●).

Figure 5:
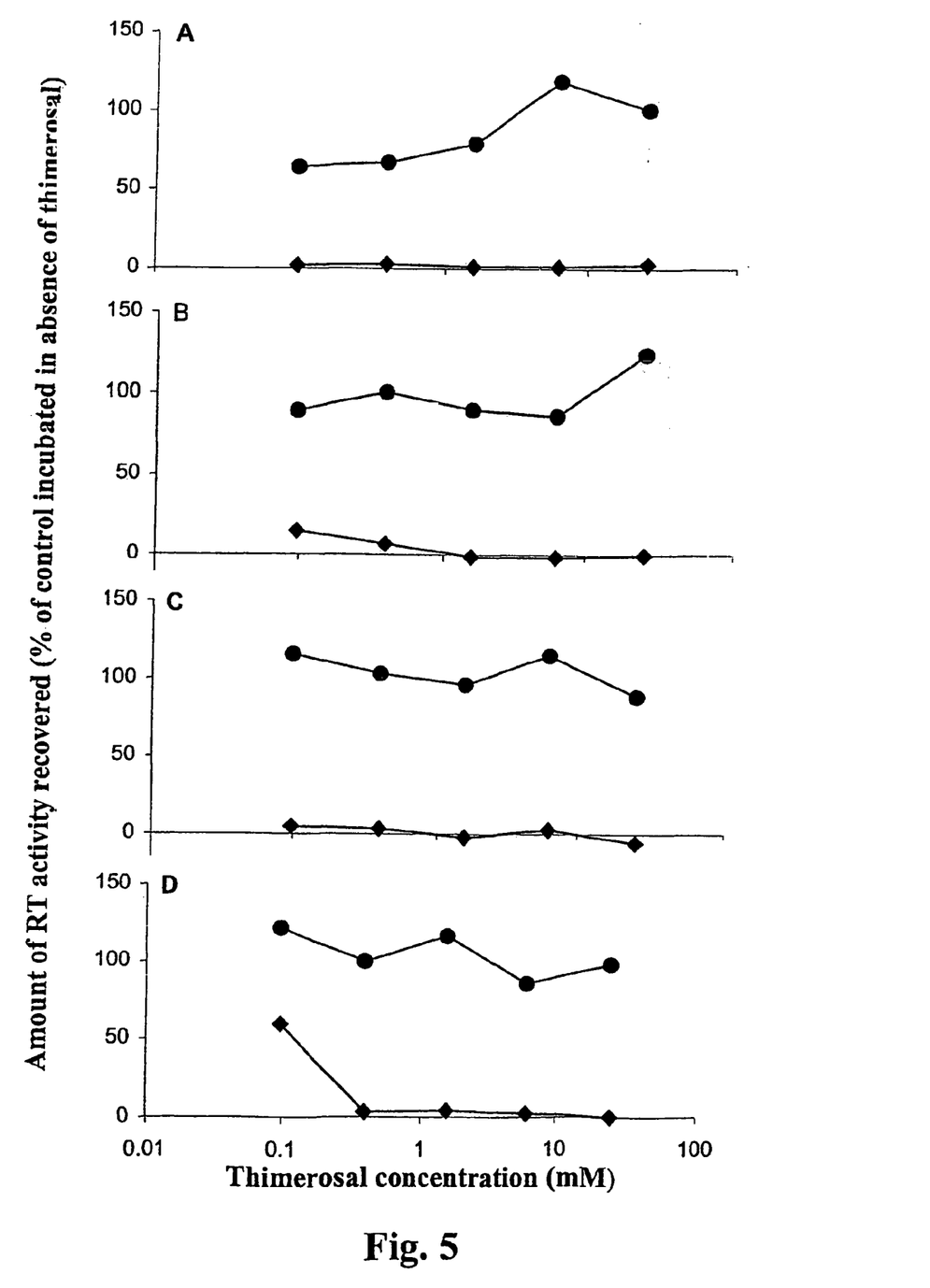
FIG. 5 shows diagrams of alternative protocols for treatment of plasma samples from HIV infected patients. The polymerase inactivation step in protocol I was performed: A) In a separate incubation. B) During the same step as the virion binds to the gel. C) As in B but the gel was stored with the substance. D) As in C but the gel was washed prior to use. Plasma RT activity (◆), HIV RT activity (●).

All four alternatives were found useful, i.e. the plasma RT activity was inactivated without affecting the HIV RT activity, but the amount of substance required for quantitative elimination of the human plasma polymerase activity varied.

Example 8

Resurrection of Plasma Polymerase Activity after Treatment with Different Cysteine-modifying Agents A set of human plasma samples (60% plasma in water) was first incubated with 3 mM of indicated cysteine-modifying substance or water (as control) at room temperature for 1 hour. Serial dilutions of five potentially reactivating substances were then added and the samples were incubated for another hour. Each sample was finally diluted 1:20 and residual RT activity was determined with Cavidi® HS kit Lenti RT. The total reduction in substance concentration between sample incubation and RT assay was 200 times. The RT activities recovered were recalculated into percent of the activity of a control consisting of plasma incubated in absence of additions during both incubation steps. The results are listed in Table 3.

All three cysteine-modifying agents tested had the capacity to totally inactivate the plasma RT activity. There was, however, a clear difference in the conditions required to reactivate polymerase activity which had been treated with different agents. Enzyme treated with Thimerosal was quite easily reactivated while enzyme treated with 5,5'-Dithiobis-(2-nitrobenzoic acid) or Chloramine T required strongly reductive low molecular weight thiols for activation.

From Table 3 is also evident that it is essential not to use too strong antagonistic substances to inactivate the polymerase modifying agent. There is a risk to reactivate the plasma polymerase!

Example 9

Quantification of Viral RT in Samples with High Endogenous RT Activity Without Purification A) EDTA plasma from a healthy blood donor, B) FIV virus diluted in inactivated FCS (devoid of RT activity) or C) in Dulbeco minimal essential medium with 5% FCS were diluted 1:1 and incubated with indicated concentration of 5,5'-dithiobis-(2-nitrobensoic acid) for one hour at room temperature (20° C.). Each sample was then serially diluted in fourfold steps in conditioning buffer (B). Cysteamine to a final concentration of 20 mM was then added to all samples and the set was incubated for another hour at room temperature. The RT activity of each sample was then determined using Cavidi® HS kit Lenti RT. 15 μl of each sample was added to 135 μl reaction mixture giving a final cysteamine concentration in assay of 2 mM. The RT activity recovered at the three first dilutions corresponding to 7.5, 1.9 and 0.5 μl sample per RT assay was recalculated into percentage of a control incubated in absence of substance and plotted against the substance concentration, see FIG. 6.

Figure 6:
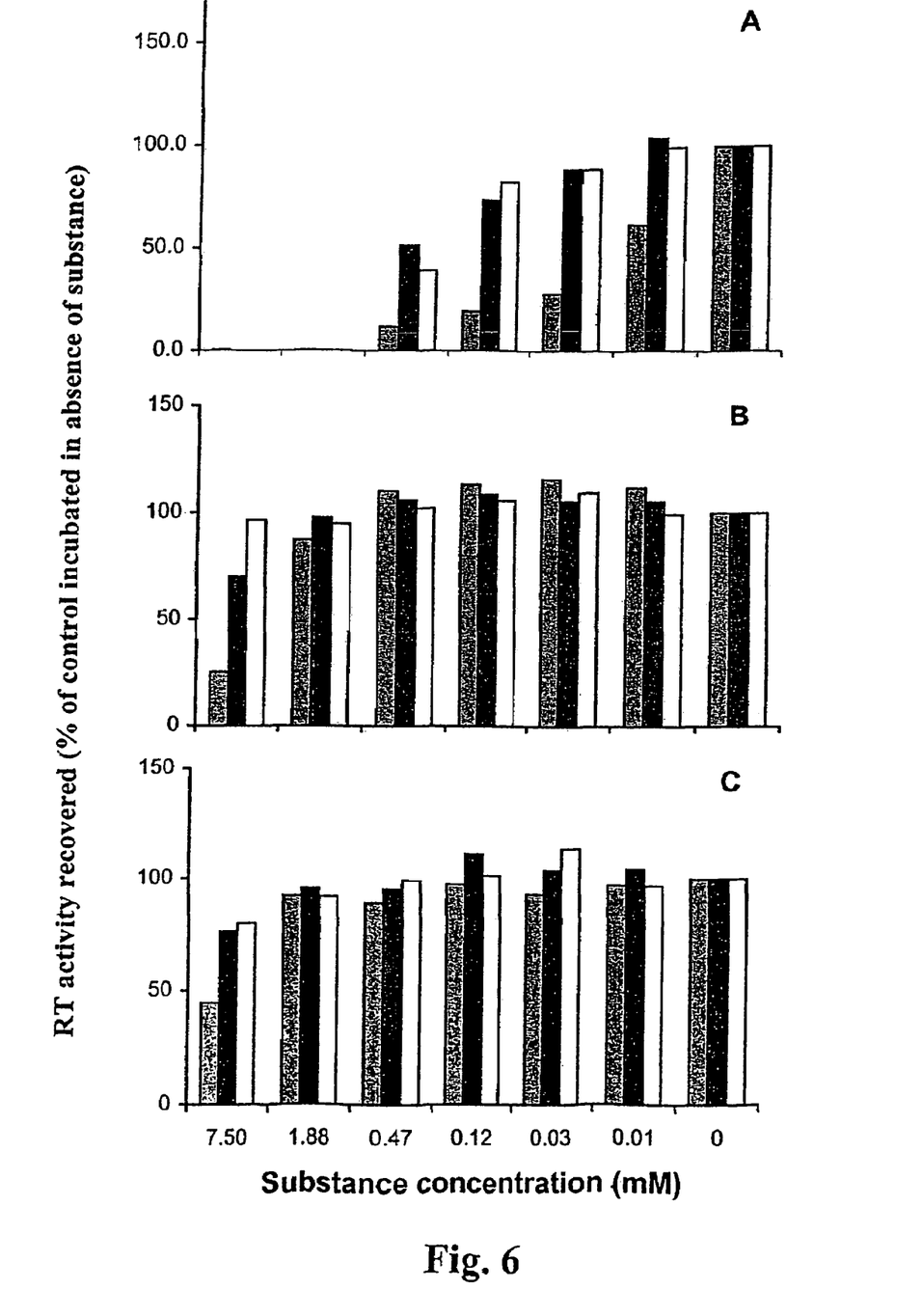
FIG. 6 shows diagrams of quantification of viral RT in samples with high endogenous RT activity without purification. EDTA plasma from a healthy blood donor (A), FIV virus in inactivated FCS (B) and in cell culture medium (C).

The human plasma polymerase activity was eliminated after incubation with 5,5'-dithiobis-(2-nitrobensoic acid) concentrations above 0.47 mM. The recovery of FIV virus RT was not adversely affected by incubation with substance concentrations below 1.88 mM. FIV RT can thus be measured selectively in crude samples after incubation with 5,5'-dithiobis-(2-nitrobensoic acid) in a concentration range around 2 mM.

TABLE 1

Some characteristics of an unidentified RT activity from human plasma

| Addition of indicated component | Amount of odT (ng) | Activity of indicated enzyme in RT assay (%) | | | |
|---|---|---|---|---|---|
| | | HIV | FIV | plasma 1 | plasma 2 |
| none | 0 | 0 | 0 | 0 | 0 |
| none | 3 | 95 | 93 | 47 | 51 |
| none* | 12 | 100 | 100 | 100 | 100 |
| KCl (0.1 M)$^a$ | 12 | 87 | 110 | 17 | 20 |
| ddTTP (2.5 $10^{-6}$ M)$^a$ | 12 | 18 | 28 | 7 | 9 |
| ddCTP (2.5 $10^{-6}$ M)$^a$ | 12 | 89 | 75 | 94 | 103 |
| ddGTP (2.5 $10^{-6}$ M)$^a$ | 12 | 94 | 93 | 103 | 109 |
| ddATP (2.5 $10^{-6}$ M)$^a$ | 12 | 90 | 79 | 94 | 105 |
| PFA (1 mM)$^a$ | 12 | 1 | ND | 92 | 94 |

*Reference condition giving 100% RT activity
$^a$Final concentration in RT assay
PFA = trisodium phosophonoformate

TABLE 2

Substances with capacity to destroy human plasma RT activity

| Substance name | Effect on plasma RT $ED_{50}$ (mM)* | Recovery of HIV virion RT (%)$^a$ |
|---|---|---|
| Phenylmercuric acetate | 0.11 | 69 |
| Thimerosal | 0.25 | 130 |
| p-Hydroxymercuribenzoate | 0.12 | 72 |
| N-etylmalemide | 0.18 | 157 |
| 5,5'-Dithiobis-(2-nitrobenzoic acid) | 0.018 | 120 |
| 2-Aminoethyl 2'-aminoethanethiolsulfonate | 0.18 | 112 |
| 2,2'-Dithiodipyridine | 0.04 | 100 |
| 2-Nitro-5-thiocyanobenzoic acid | 0.2 | 72 |
| Methyl methane-thiosulfonate | 0.1 | 84 |

*$ED_{50}$ Efficient dose 50. The substance concentration required to reduce the plasma RT activity by 50%.
$^a$Recovery of HIV RT from virions in human plasma incubated with 5 mM of indicated substance and purified according to protocol I.

TABLE 3

Resurrection of plasma polymerase activity after treatment with cysteine-modifying agents.

| Destroying agent in first incubation | Polymerase activity after second incubation with indicated substance (% of control[a]) | | | | | |
|---|---|---|---|---|---|---|
| | Concentration (mM) | cysteine | cysteamine | DTT[b] | MSA[c] | glutathione | water |
| None | 30 | 198 | 6 | 860 | 7 | 13 | 100 |
| | 10 | 145 | 6 | 767 | 64 | 80 | 100 |
| | 3.3 | 82 | 9 | 613 | 110 | 78 | 100 |
| | 1.1 | 72 | 15 | 260 | 109 | 72 | 100 |
| 3 mM Thimerosal | 30 | 68 | 1 | 448 | 3.4 | 7 | 0 |
| | 10 | 37 | 2 | 377 | 7.3 | 37 | 0 |
| | 3.3 | 14 | 0 | 248 | 19 | 21 | 0 |
| | 1.1 | 4 | 0 | 84 | 17 | 12 | 0 |
| 3 mM DNBA[d] | 30 | 7 | 1 | 122 | 0 | 2 | 0 |
| | 10 | 0 | 0 | 143 | 0 | 1 | 0 |
| | 3.3 | 1 | 0 | 1 | 0 | 0 | 0 |
| | 1.1 | 0 | 0 | 0 | 0 | 0 | 0 |
| 3 mM Chloramine T | 30 | 9 | 0 | 94 | 0 | 0 | 0 |
| | 10 | 4 | 0 | 80 | 1 | 3 | 0 |
| | 3.3 | 2 | 0 | 51 | 0 | 0 | 0 |
| | 1.1 | 1 | 0 | 2 | 6 | 0 | 0 |

[a]Control incubated in absence of destroying agent.
[b]Dithiothreitol.
[c]Mercaptosuccinic acid.
[d]5,5'-dithiobis-(2-nitrobenzoic acid).

REFERENCES

Baltimore D, Smoler D (1971) Primer requirement and template specificity of the DNA polymerase of RNA tumor viruses. *PNAS* 68, 1507-11

Ekstrand D. H. L., Awad R. J-K., Källander C. F. R. and Gronowitz J. S. (1996) A sensitive assay for the detection and quantification of RT activity, based on the use of carrier bound template and non-radioactive product detection, with special reference to HIV isolation. *Biotechnology and Applied Biochemistry.*23, 95-105.

Gatu T, Gronowitz J. S., Källander C., Malmsten A., Petterson I.(2000) Methods of concentrating and recovering a viral enzyme activity from biological samples. PCT/SE01/00617, filed on Mar. 22, 2001.

Goulian M, Grimm S L. (1990) Three cytoplasmic DNA polymerases that utilize poly(rA).oligo(dT). Biochem Biophys Res Commun.170:627-34.

Hizi A, Shaharabany M, Tal R, Hughes. (1992) The effects of cysteine mutations on the reverse transcriptases of human immunodeficiency virus types 1 and 2. J Biol Chem. 267: 1293-7.

Hübscher U, Nasheuer H P, Syvaoja J E. (2000) Eukaryotic DNA polymerases, a growing family. Trends Biochem Sci. 25:143-7. Review.

Lee M, Sano K., Morales F. E., and D. T. Imagawa. (1987) Sensitive reverse transcriptase assay to detect and quantitate human immunodeficiency virus. J.Clin.Microbiol. 25:1717-21.

Means G E, Feeney R E. (1990) Chemical modifications of proteins: history and applications. Bioconjug Chem. 1(1): 2-12.

Yoshida S, Masaki S, Koiwai O. (1981) Further characterization of a poly(rA) oligo(dT)-dependent activity of multiple DNA polymerase alpha from calf thymus. Biochim Biophys Acta. 654:194-200.

The invention claimed is:

1. Method of recovering a retroviral reverse transcriptase (RT) activity from enveloped retroviruses in a biological sample containing non-protected cellular polymerases, comprising the steps of a) incubating the biological sample with a cysteine-modifying agent selected from the group consisting of N-ethylmalemide, Thimerosal, p-hydroxymercuribenzoate, 5,5'-dithiobis-(2-nitrobenzoic acid), 2-aminoethyl 2'-aminoethanethiolsulfonate, 2-nitro-5-thiocyanobenzoic acid, methyl methane-thiosulfonate, phenylmercuric acetate and 2,2'-dithiodipyridine, to destroy the activity of contaminating cellular polymerases while preserving retroviral RT activity within the virus envelope, b1) removing the enveloped virus particles from the incubation mixture using a virus binding matrix and a washing step, or b2) inactivating the cysteine-modifying agent with an inactivating substance while preserving the virus envelope from lysis, c) lysing the virus envelope with a lysing buffer to release the virus enzymes, and d) recovering the released retroviral RT enzyme from the lysing buffer.

2. Method according to claim 1, wherein virus is selected from Lentiviruses, HTLV/BLV viruses, mammalian D-type retrovirus and mammalian C-type retrovirus.

3. Method according to claim 2, wherein the Lentivirus is human immunodeficiency virus (HIV).

4. Method according to claim 1, wherein the biological sample is a sample of body fluid.

5. Method according to claim 4, wherein the sample of body fluid is a blood, plasma or serum sample.

6. Method according to claim 1, wherein the inactivating substance is a mild reducing agent.

7. Method according to claim 6, wherein the mild reducing agent is selected from the group consisting of cysteine, cysteamine, mercaptosuccinic acid, and glutathione.

8. The method of claim 1, which comprises removing the enveloped virus particles from the incubation mixture using a virus binding matrix and a washing step, the virus is human immunodeficiency virus (HIV), the biological sample is a sample of body fluid and the virus-binding matrix is an anion exchanger matrix.

9. The method of claim 1, which comprises inactivating the cysteine-modifying agent with an inactivating substance while preserving the virus envelope from lysis, the virus is human immunodeficiency virus (HIV), the biological sample is a sample of body fluid and the wherein the inactivating substance is a mild reducing agent selected from the group consisting of cysteine, cysteamine, mercaptosuccinic acid, and glutathione.

* * * * *